United States Patent
Poucher et al.

(10) Patent No.: US 9,750,574 B2
(45) Date of Patent: Sep. 5, 2017

(54) SURGICAL SYSTEM FOR AND A METHOD OF IDENTIFYING AN INCISION SITE

(71) Applicant: Coloplast A/S, Humlebaek (DK)

(72) Inventors: Neal Poucher, North Oaks, MN (US); Fernando El-Hage, Brooklyn Park, MN (US)

(73) Assignee: Coloplast A/S, Humlebaek (DK)

( * ) Notice: Subject to any disclaimer, the term of this patent is extended or adjusted under 35 U.S.C. 154(b) by 317 days.

(21) Appl. No.: 14/288,392

(22) Filed: May 28, 2014

(65) Prior Publication Data

US 2015/0342687 A1  Dec. 3, 2015

(51) Int. Cl.
| | |
|---|---|
| *A61B 5/06* | (2006.01) |
| *A61F 2/00* | (2006.01) |
| *A61B 19/00* | (2006.01) |
| *A61B 1/00* | (2006.01) |
| *A61B 5/20* | (2006.01) |
| *A61B 5/00* | (2006.01) |
| *A61B 90/11* | (2016.01) |
| *A61B 34/00* | (2016.01) |
| *A61B 90/00* | (2016.01) |

(52) U.S. Cl.
CPC .......... *A61B 19/22* (2013.01); *A61B 1/00158* (2013.01); *A61B 5/062* (2013.01); *A61B 5/202* (2013.01); *A61B 5/4375* (2013.01); *A61B 34/70* (2016.02); *A61B 90/11* (2016.02); *A61B 2034/733* (2016.02); *A61B 2090/3937* (2016.02); *A61F 2/0036* (2013.01)

(58) Field of Classification Search
CPC ..... A61B 5/061–5/062; A61B 1/00158; A61N 2/06
USPC .......................................................... 600/12
See application file for complete search history.

(56) References Cited

U.S. PATENT DOCUMENTS

| | | | | | |
|---|---|---|---|---|---|
| 3,426,758 | A | * | 2/1969 | Haraituneian | ....... A61M 25/10 116/1 |
| 3,961,632 | A | * | 6/1976 | Moossun | ............ A61J 15/0015 128/DIG. 26 |
| 4,063,561 | A | * | 12/1977 | McKenna | ............. A61M 16/04 128/207.15 |
| 4,850,963 | A | * | 7/1989 | Sparks | .................. A61F 2/0004 128/899 |
| 5,489,269 | A | * | 2/1996 | Aldrich | ............. A61B 17/3415 604/540 |

(Continued)

FOREIGN PATENT DOCUMENTS

| | | |
|---|---|---|
| WO | 9956813 A1 | 11/1999 |
| WO | 2011076211 A1 | 6/2011 |

*Primary Examiner* — Catherine B Kuhlman
(74) *Attorney, Agent, or Firm* — Coloplast Corp., Coloplast A/S; Nick Baumann

(57) ABSTRACT

A surgical system for and a method of identifying an incision site includes a surgical system having an intra-urethral probe and a template. The probe has a distal end opposite of a proximal end that is insertable into a urethra of a patient. The probe is sized and configured to prevent the proximal end of the probe from entering a bladder of the patient. A proximal end portion of the probe is magnetized to a first polarity. The template is sized for placement between an anus and a scrotum of the patient. The template includes a magnetic region magnetically attractable to the first polarity of the probe.

3 Claims, 13 Drawing Sheets

(56) References Cited

U.S. PATENT DOCUMENTS

| | | | | | |
|---|---|---|---|---|---|
| 5,569,237 | A | * | 10/1996 | Beckenstein | A61B 19/54 604/116 |
| 5,971,967 | A | * | 10/1999 | Willard | A61M 25/04 600/29 |
| 6,173,199 | B1 | * | 1/2001 | Gabriel | A61J 15/00 128/899 |
| 2004/0231683 | A1 | * | 11/2004 | Eng | A61B 1/00158 128/899 |
| 2009/0018533 | A1 | * | 1/2009 | Perkins | A61B 18/04 606/14 |
| 2009/0076502 | A1 | * | 3/2009 | Azure | A61B 18/1485 606/41 |

* cited by examiner

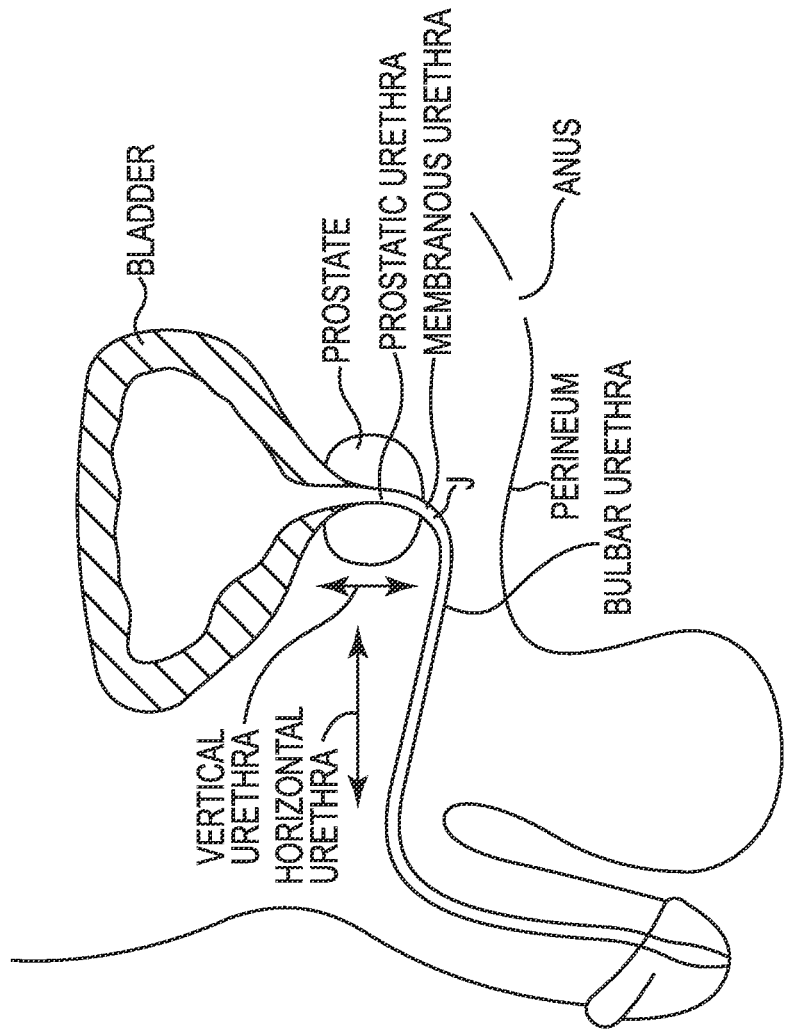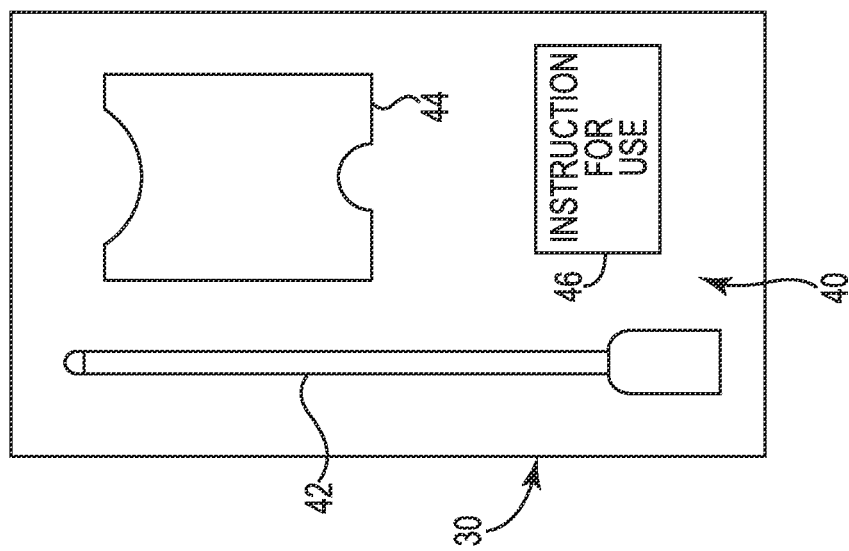
Fig. 2

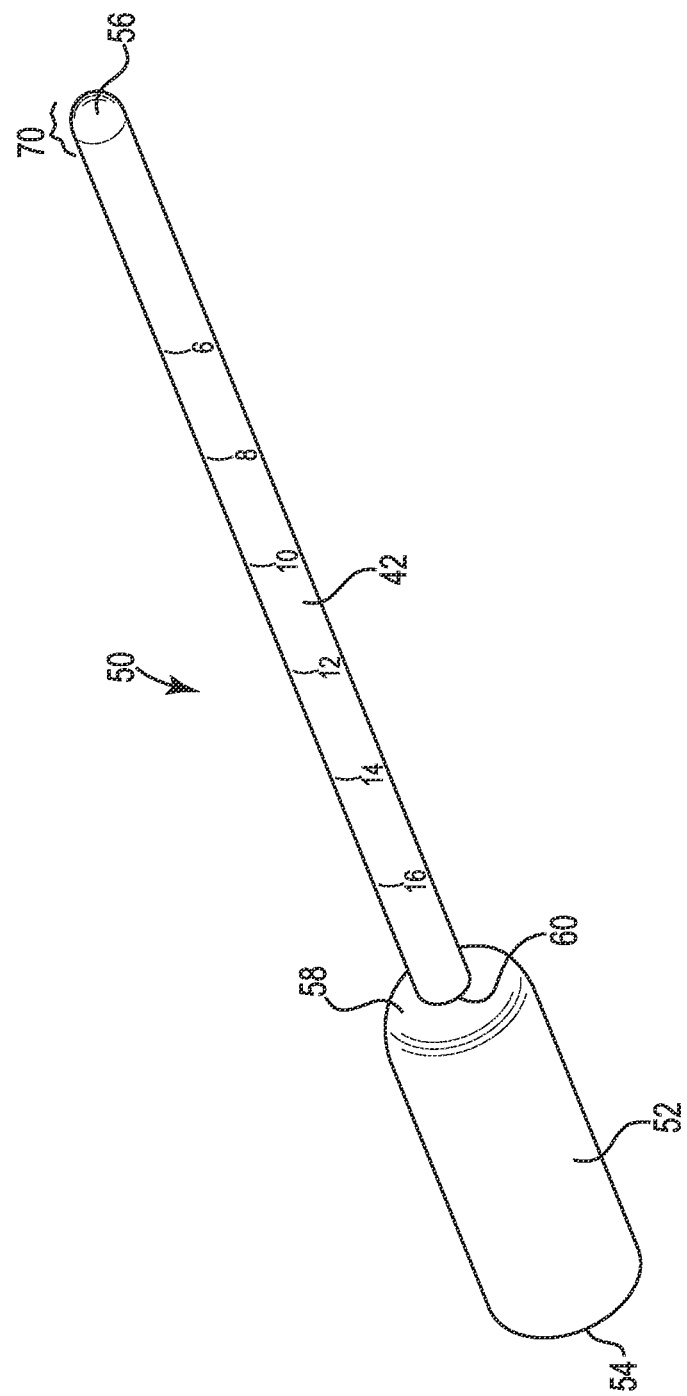

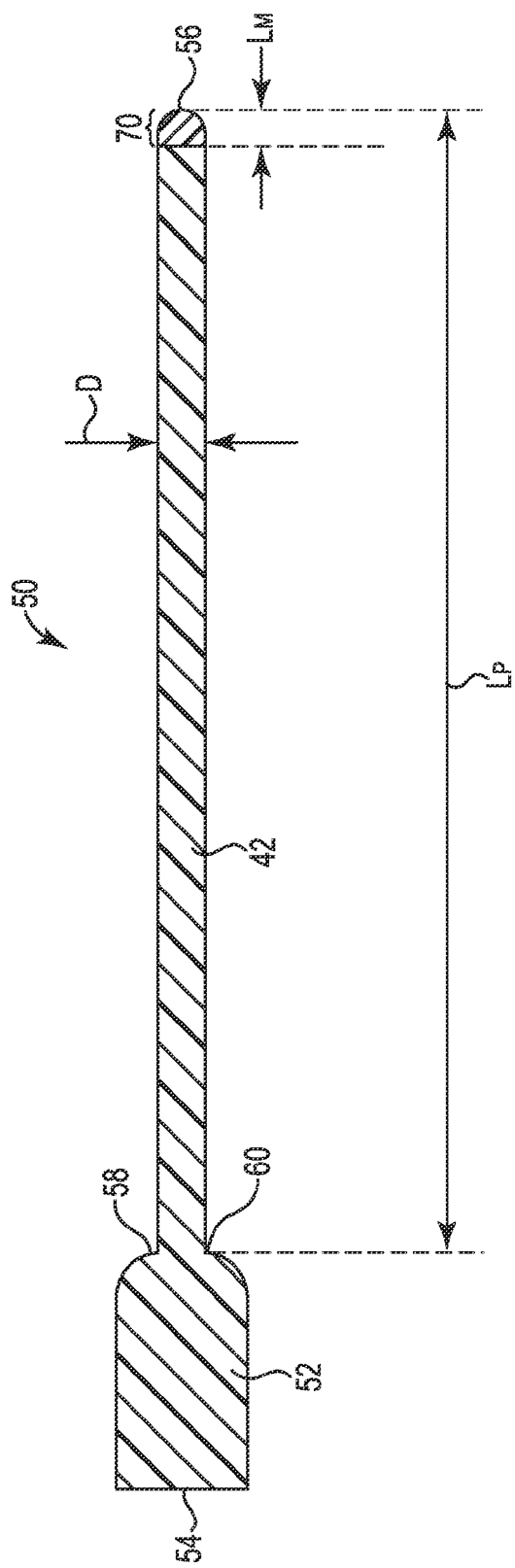
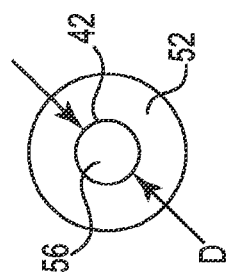

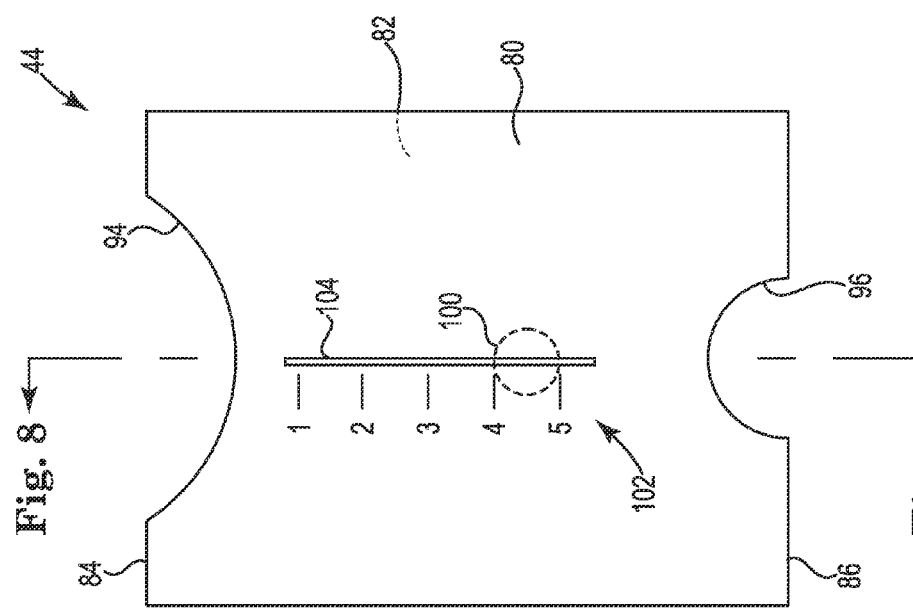

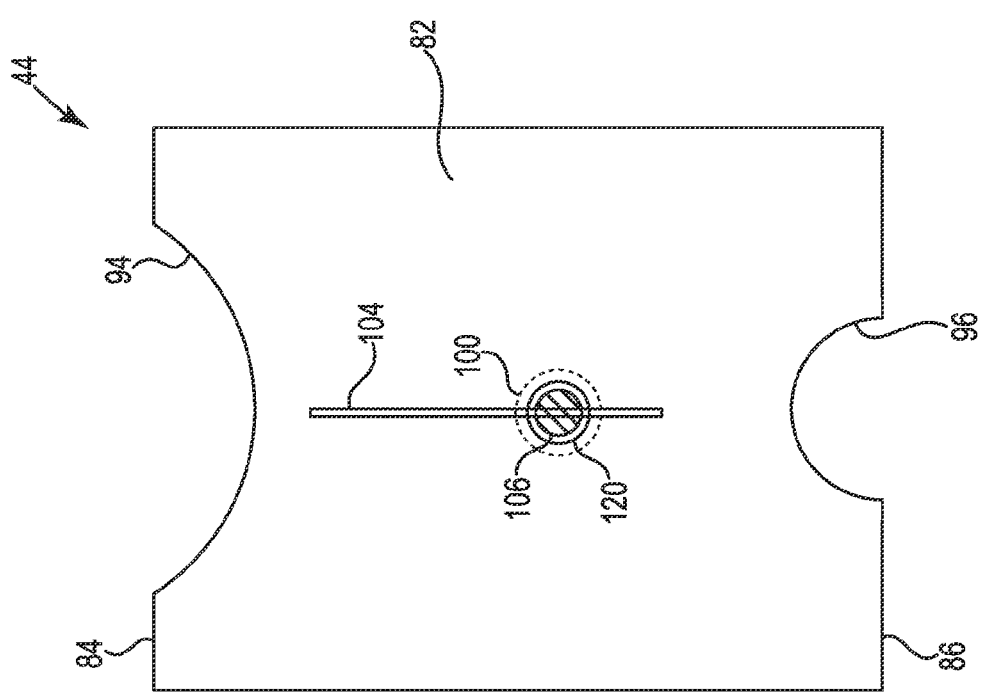

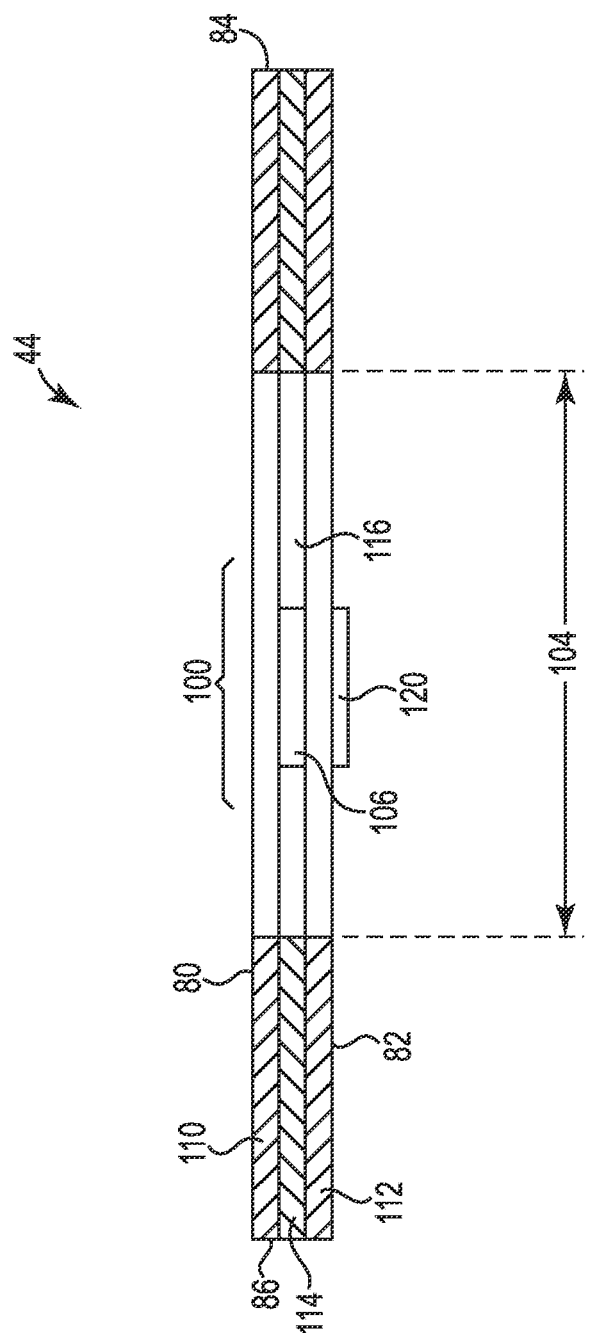

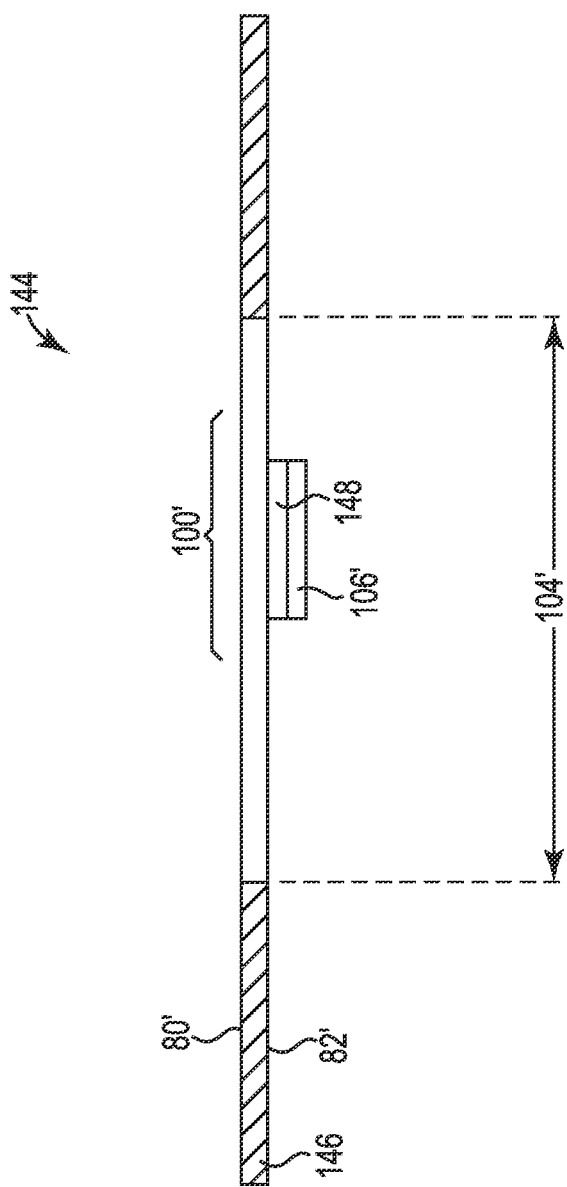

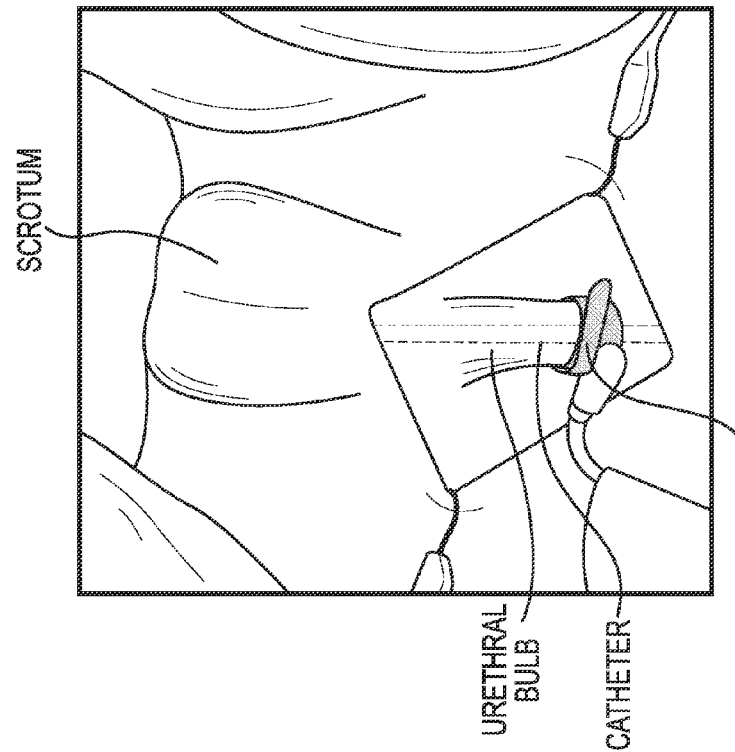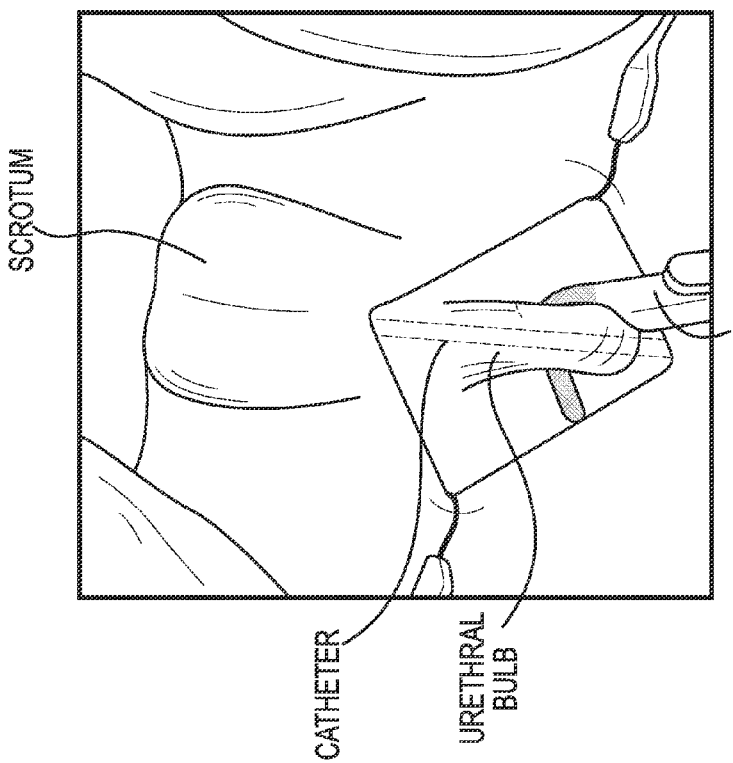

SURGICAL SYSTEM FOR AND A METHOD OF IDENTIFYING AN INCISION SITE

BACKGROUND

Urinary incontinence affects many people and is a worldwide health issue. Published research indicates that urinary incontinence presents a substantial social and economic burden worldwide, affecting up to a mean of about 16% of the global population.

Urinary incontinence in women can be associated with a prolapse of one or more pelvic organs, which can arise from child birth or a weakness in the tissues/muscle of the pelvic floor. Urinary incontinence in men can arise after surgical treatment of the prostate glade, which treatment can include removal or weakening of the prostatic sphincter of the urinary urethra.

One treatment for urinary incontinence includes placing an artificial sphincter around a circumference of a portion of the urethra. The artificial sphincter operates to compress the urethra to selectively coapt or stop the flow of urine through the urethra, thus providing the user with a continent state. The artificial sphincter can be activated to an open position by the user, which opens the urethra and allows the user to selectively pass urine.

Surgeons and patients would welcome advances in the treatment of urinary incontinence.

SUMMARY

One aspect provides a surgical system adapted for identifying an incision site. The surgical system includes an intra-urethral probe and a template. The intra-urethral probe has a proximal end opposite of a distal end that is insertable into a urethra of a patient. The intra-urethral probe is sized and configured to prevent the distal end of the intra-urethral probe from entering a bladder of the patient. A distal end portion of the intra-urethral probe is magnetized to a first polarity. The template is sized for placement between an anus and a scrotum of the patient. The template has a magnetic region magnetically attractable to the first polarity of the intra-urethral probe.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2 is a schematic view of one embodiment of male anatomy and a kit of parts providing a surgical system adapted for identifying an incision site on the man.

FIG. 3 is a perspective view of one embodiment of an intra-urethral probe.

FIG. 4 is a cross-sectional view and FIG. 5 is an end view of the intra-urethral probe illustrated in FIG. 3.

FIG. 6 is a top view of one embodiment of a template of the system illustrated in FIG. 2.

FIG. 7 is a bottom view of the template illustrated in FIG. 6.

FIG. 8 is a cross-sectional view of the template illustrated in FIG. 6.

FIG. 9 is a cross-sectional view of one embodiment of a template suitable for use with the surgical system illustrated in FIG. 2.

FIGS. 13-15 are schematic views a perineal incision formed in the male anatomy.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

The features of the various exemplary embodiments described in this application may be combined with each other ("mixed and matched"), unless specifically noted otherwise.

Soft tissue includes dermal tissue, sub-dermal tissue, ligaments, tendons, or membranes but does not include bone.

The term "anterior" in this application means front, as in forward, and the term "posterior" means back, as in rearward. For example, the chin is anterior and the shoulder blade is posterior on the human anatomy.

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the prostate of the patient.

A surgical tool has a distal end that is insertable into a urethra of a patient, as taken in reference to the surgeon handling a proximal end of the tool.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion adjacent to the first end and another end portion adjacent to the second end.

Artificial urinary sphincters have proved useful in the treatment of urinary incontinence. An artificial urinary sphincter is implanted around the urethra and is operable to selectively coapt the lumen in the urethra to allow the user to shift the sphincter from an open state that allows urine to pass a closed state that provides the user with a continent state.

Figure 1:
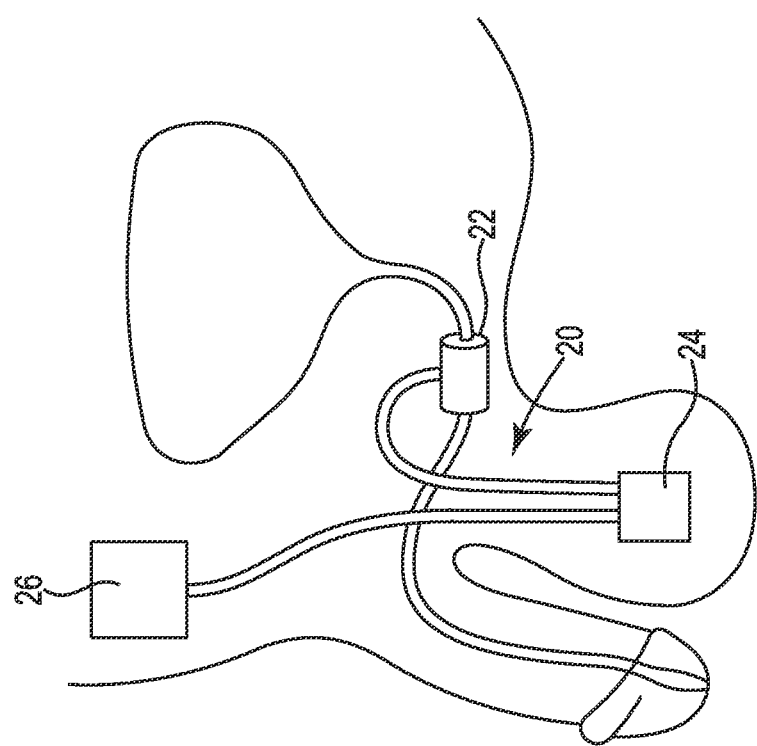
FIG. 1 is a perspective view of a prior art artificial urinary sphincter (AUS) system implanted in the urogenital region of a male patient.

FIG. 1 is a perspective view of a prior art artificial urinary sphincter (AUS) system 20 implanted in the urogenital region of a male patient. The AUS system 20 includes three components cooperatively attached with tubing: an occlusive cuff 22, a control pump 24, and a pressure-regulating balloon reservoir 26. The cuff 22 is implanted around the urethra. The control pump 24 is implanted in the scrotum of a male user. The pressure-regulating balloon reservoir 26 is implanted in the prevesical space, for example somewhere in the abdomen.

During implantation of the AUS 20, the surgeon will generally form a perineal incision to access the urethra distal of the bladder. Tissue is dissected around the circumference of the urethra to create a space that allows for the placement of the cuff 22 around the urethra.

The male anatomy includes a bend or a junction in the urethra where the urethra transitions from a horizontal orientation extending generally along the length of the penis to a vertical orientation that connects with the bladder. Each man can have a slightly different location for the bend in the urethra. Surgeons prefer to place the cuff of an AUS near the bend in the urethra or immediately distal to the bend in the urethra as this location (referred to as the bulbar urethra) is associated with favorable muscle mass around the urethra.

Embodiments provide a kit of parts and a system that is useful for identifying an incision site in the perineum of a male patient, where the incision site is located on the skin at or immediately distal the bend in the urethra. Forming an incision at the located incision site allows the surgeon improved and more accurate access to the bulbar urethra, with less dissection of tissue.

Embodiments provide a surgical system adapted for consistently and repeatably identifying the natural bend in the urethra for each individual patient. After the natural bend in the urethra is identified the surgeon will access that targeted area through an incision formed in the perineal skin. The system includes an intra-urethral probe having a distal end that is insertable into a urethra to identify and locate the natural bend in the urethra and a template operable to sense the location of the distal end of the inserted probe and identify the incision site on the skin.

FIG. 2 is a schematic view of one embodiment of a kit 30 of parts providing a surgical system 40 adapted for identifying an incision site in the male anatomy. The surgical system 40 includes an intra-urethral probe 42 (probe 42), a template 44, and instructions 46 for use of the probe 42 and the template 44.

With reference to the male anatomy illustrated in FIG. 2, it is desirable to place the cuff of an AUS around that portion of the horizontal urethra that is closest to the bladder, in part because this section of the anatomy is where the most muscle mass resides in relation to the urethra. Some patients have had all or a portion of their prostate removed. Removal of the prostate can weaken or diminish the functionality of the sphincter located in the prostatic urethra. The prostatic urethra is located in that section of the urethra that descends in a vertical orientation away from the bladder, and the prostatic urethra may or may not include a functioning sphincter. The bulbar urethra is located in that section of the urethra that extends in a horizontal orientation away from the location of the prostate or prostatic urethra. The horizontal section of the bulbar urethra extends to the pendulous urethra that exits out of the penis.

The surgeon desires to place the cuff of the AUS around the bulbar urethra immediately distal a junction J where the vertical prostatic urethra has a bend that transitions to the horizontal bulbar urethra. In other words, the surgeon desires to place the cuff of the AUS at the bulbar urethra immediately distal the prostatic urethra (and immediately distal the junction J). Locating this junction in the urethra is a challenge. Specifically, locating the site on the perineum to form the incision to access the bulbar urethra presents a challenge to some surgeons, as the location of the horizontal/vertical junction J of the urethra is somewhat different for each individual.

The probe 42 is rigid, and sized and shaped to be inserted a distance in the horizontal section of the urethra until the junction J where urethra bends or transitions to its vertical orientation. The probe 42 does not bend along the urethra as would an intermittent catheter, and thus the probe 42 does not enter the bladder. Instead, when inserted, a distal-most end the probe 42 indicates the location of the junction J where the urethra transitions from the horizontal orientation to the vertical orientation since the probe 42 is unable to make the transition in this curvature of the urethra. The template 44 is configured to communicate with the probe 42 to mark the location on the perineal skin that corresponds with the location of the distal-most end of the probe 42. The surgeon follows this mark of the location on the perineal skin in determining and identifying the incision site for implantation of the AUS.

FIG. 3 is a perspective view, FIG. 4 is a cross-sectional view, and FIG. 5 is an end view of a surgical tool 50. The surgical tool 50 includes a handle 52 attached to the intra-urethral probe 42. In one embodiment, the surgical tool 50 extends from a proximal end 54 provided by the handle 52 to a distal end 56 provided by the probe 42, with a distal end 58 of the handle 52 attached to a proximal end 60 of the probe 42. A distal end portion 70 of the probe 42 includes a magnet that magnetizes the distal end portion 70 and the distal end 56 of the probe 42 to a first polarity.

The distal end 56 of the probe 42 is sized to be insertable into the urethra of the patient. The probe 42 is configured to resist bending in a manner that prevents the distal end 56 from entering a bladder of the patient. That is to say, the probe 42 lacks the flexibility to follow the bend in the urethra that transitions from the horizontal section of the urethra to the vertical section of the urethra. The probe 42 has a rigidity that is selected to prevent the probe 42 from bending, and in combination with the size of the probe 42, this prevents the distal end 56 of the probe 42 from traversing the curved portion of the urethra.

FIG. 3 illustrates that the probe 42 has a length Lp extending from the proximal end 60 to the distal end 56, where the length Lp is selected to be less than a length of the male urethra, for example less than about 16 cm. One approach includes fabricating the probe 42 to have a length that is shorter than most male urethras to prevent the distal end 56 of the probe 42 from entering the bladder of the patient.

In one embodiment, the distal end portion 70 of the probe 42 extends a distance Lm in a proximal direction from the distal end 56, where Lm is less than about 25% of the length Lp of the probe 42. At least the distal end 56 of the distal end portion 70 of the probe 42 is magnetized. It is desirable to configure the distal end portion 70 in a manner that will "pinpoint" a location of the distal end 56 of the inserted probe 42 since the distal end 56 extends into the urethra only so far as the junction J (FIG. 2). In some embodiments, the distance Lm of the distal end portion 70 of the probe 42 is less than about 15% of the length Lp of the probe 42, or between 1-10% of the length Lp of the probe 42, and preferably the distance Lm of the distal end portion 70 of the probe is between 1-5% of the length Lp of the probe 42.

The probe 42 is provided with a diameter D that is small enough to allow the probe 42 to be inserted into the urethra and large enough to prevent the probe 42 from traversing the curvature in a urethra (at the junction J of the urethra) and entering the bladder. In one embodiment, the diameter D of the probe 42 is in a range from 5-15 mm and is sized to prevent the distal end 56 of the probe 42 from entering the bladder of the patient.

The flexural modulus is a ratio of measured stress to strain during a flexing deformation. The flexural modulus characterizes the tendency of a material to bend. The flexural modulus is determined from the slope of the stress-strain curve produced during a flexural test, such as provided for and described in standard test ASTM D 790. The units of flexural modulus is force per area represented as pounds per square inch (psi). In one embodiment, the probe 42 has a rigidity selected to prevent the probe 42 from bending along the curvature of the urethra. In one embodiment, the probe 42 is a flexural modulus of greater than 50,000 psi. One suitable range for the flexural modulus of the probe 42 is between 50,000-250,000 psi, with one suitable flexural modulus being about 100,000 psi. As comparative examples, polyethylene has a flexural modulus of about 101,500 psi and polypropylene flexural modulus of about 217,500 psi. Flexural moduli above 250,000 psi are acceptable as this material will be stiffer and more resistant to bending, which will contribute to preventing the probe 42 from advancing past the curved portion of the urethra leading to the bladder.

The probe 42 could be fabricated from a ferromagnet such as an iron-based metal that responds to the magnet in the template 44, but iron is considered to be not well suited for use in open surgical procedures due to its propensity to rust. Mindful of this, suitable materials for the fabrication of the probe 42 include materials that can be bonded to or modified to include a permanent magnet at the distal end portion 70 or at the end 56. These suitable materials include stainless steel, a high density polyethylene, polypropylene, a coating of a polymer over a stainless steel rod, or a hydrophilic coating applied to a metal rod to provide the metal rod with a lubricious surface having reduced friction when in contact with the urethral tissue.

In one embodiment, the distal end portion 70 is provided by a permanent rare earth magnet that is bonded to the probe 42 to provide at least the end 56 with magnetic properties.

FIG. 6 is a front view, FIG. 7 is a back view, and FIG. 8 is a cross-sectional view of the template 44.

The template 44 has a front face 80 opposite a back face 82, where the faces 80, 82 extend between an anterior end 84 and a posterior end 86. In one embodiment, an anterior edge 94 is curved to provide a recess that is sized to fit around the base of the scrotum, and a posterior edge 96 is curved to provide a recess that is sized to fit around a portion of the anus. The front face 80 is oriented in a direction toward the surgeon and the back face 82 is suitable for placement onto the perineal skin between the scrotum and the anus.

The template 44 includes a magnetic region 100 located on a central longitudinal axis between the anterior end 84 and the posterior end 86. In one embodiment the magnetic region 100 is centered between the lateral edges of the template 44. The magnetic region 100 includes or surrounds a magnet that is magnetized to a polarity that attracts the first polarity of the end 56 of the intra-urethral probe 42. For example, the polarity of the end 56 of the intra-urethral probe 42 is suitably magnetized to include a +N+ polarity and the polarity of a magnetic region 100 is suitably magnetized to include a −S− polarity that is attracted to the N+ polarity.

The magnetic region 100 is magnetically attracted to the end 56 of the intra-urethral probe 42. The probe 42 is configured to not bend and to resist advancing when the probe 42 is advanced in the urethra to a proximal location of the junction J where the urethra bends from the horizontal position to the vertical position. Magnet attraction of the magnetic region 100 (exterior the patient) to the end 56 of the intra-urethral probe 42 (in the urethra of the patient) thus identifies a location on the skin that corresponds to a location of the end 56 of the probe 42 at the junction J in the urethra. This skin location is the desired or optimum location for forming an incision in the perineal skin for implantation of the AUS.

In one embodiment, the template 44 includes printed indicia 102 that is useful in locating a measured distance away from the base of the scrotum, or away from the anus. In one embodiment, the printed indicia 102 is marked in the units of centimeters, although other units are also acceptable.

A magnetic region 100 of the template 44 is magnetically attracted to the end 56 of the intra-urethral probe 42 to identify the optimum location for the incision. In one embodiment, the template 44 includes an opening 104 formed through the magnetic region 100, where the opening 104 is sized to receive the blade of a scalpel, or an ink-marking pen, or other instrument used in the surgical suite. The opening 104 accommodates the placement of the incision at or within the magnetic region 100 that overlays the optimum skin location.

FIG. 7 is a top view of the back face 82 of the template 44. The back face 82 is suitable for placement in contact with the perineal tissue between the scrotum and the anus. The opening 104 extends between the front face 80 and the back face 82 and extends through the magnetic region 100. In one embodiment, the magnetic region 100 includes a magnet 106 disposed on the back face 82 of the template 44. In one embodiment, the magnetic region 100 includes a magnet 106 disposed within the layers between the front face 80 and the back face 82.

The back face 82 contacts the perineal area of the skin between the scrotum and the anus. In one embodiment, the back face 82 includes adhesive provided to secure the template 44 to the skin. The adhesive is suitably applied to a portion of the area of the back face 82, or alternatively, the adhesive is applied to the entire area of the back face 82. Suitable adhesives include a coating of acrylate adhesive, a coating of a silicone or other adhesive, or gel adhesives including hydrophilic gel adhesives that stick well to moist skin.

FIG. 8 is a cross-sectional view of the template 44. Front face 80 is provided by a first layer 110 and the back face 82 is provided by a substrate layer 112. In one embodiment, an intermediate layer 114 is disposed between the first layer 110 and the substrate layer 112. In one embodiment, the intermediate layer 114 is fabricated from a plasticize layer of magnetic material to provide at least the magnetic region 100 with magnetic properties. In one embodiment, a central intermediate layer 116 is fabricated from a plasticize layer of magnetic material to provide the magnetic region 100 with magnetic properties. The intermediate layer 114 provides a tie layer that bonds the first layer 110 to the substrate layer 112. The opening 104 extends through the thickness of the template 44 from the front face 80 to the back face 82.

At least a portion of the template 44 is magnetic. In one embodiment, the magnet 106 is a separate and discrete individualize magnet retained within the intermediate layer 116 between the first layer 110 and the substrate layer 112.

Suitable magnets for the magnetic region 100 include soft or hard ferrite magnets and rare earth magnets. Soft ferrite magnets have a low coercivity in the range of 100-200 kA/m. A permanent hard ferrite magnet is characterized as having a higher coercivity than soft ferrite magnets, with a coercivity from 200-300 kA/m. The relatively high coercivity of the hard ferrite magnet allows the magnet to resist becoming demagnetized. Rare earth magnets are permanent magnets that are formed from the lanthanide elements of metals with ferromagnetic properties. Rare earth magnets have a high coercivity in the range of 450-2000 kA/m and are characterized as having a magnetic strength of 2-5 times greater than ferrite magnets.

Suitable magnets for the intermediate layer 116 include a flexible plastic magnet formed by combining ceramic ferrite powder with a thermoplastic binder with a +N+ and –S– pole density between 2-60 poles per inch. Such flexible plastic magnets may be fabricated with a rare earth magnet molded in a flexible carrier. One suitable magnet for the magnet 106 is provided by a rare earth magnet as described above.

In one embodiment, the probe 42 is fabricated to include a permanent rare earth magnet at the distal end portion 70 and the template 44 is provided with a ferromagnetic material that is attracted to the distal end portion 70. The template 44 includes ferromagnetic materials embedded in or surrounded by the first layer 110 and the substrate layer 112 such that the ferromagnetic material is enclosed within the template and magnetically attracted to the probe 42.

In one embodiment, an ink transfer pad 120 is provided on the back face 82 and is useful for transferring ink to mark the location for the perineal incision, which is where the magnet 106 is magnetically attracted to the magnetic end 56 of the probe 42.

The template 44 is suitably fabricated from one or more layers of paper, paper-stock, cardboard, plastic, a plastic film, laminates of paper and plastic, or metal.

FIG. 9 is a cross-sectional view of one embodiment of a template 144. The template 144 is fabricated from a single layer 146 of material that provides a front face 80' opposite a back face 82'. An opening 104' is provided between the ends of the template 144, similar to the opening 104 described above. The opening 104' transects or intersects a magnetic region 100' that includes a magnet 106'. In one embodiment, the magnet 106' is adhesively attached to the back face 82' by a layer of adhesive 148. The template 144 is suitably fabricated from one or more layers of paper, paper-stock, cardboard, plastic, a plastic film, laminates of paper and plastic, or metal.

In one embodiment, the magnet 106' is a flexible plastic magnet formed as a sheet as described above such that the template 144 and the magnet 106' are integrated in a single layer.

Figure 10:
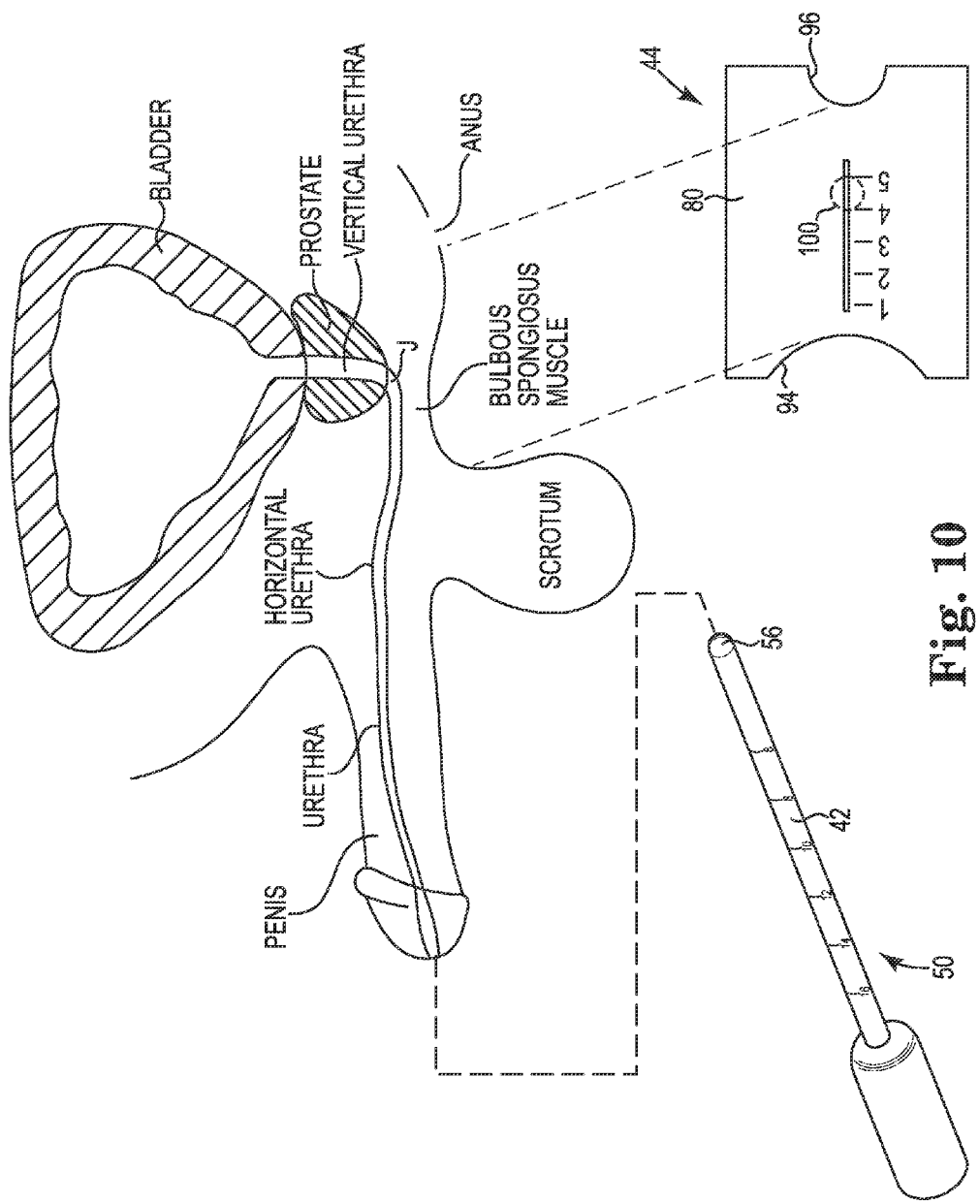
FIG. 10 is a schematic view of the intra-urethral probe and the template of the system illustrated in FIG. 2 in relationship to the male anatomy.

FIG. 10 is a schematic view of the male anatomy, the probe 42, and the template 44. The patient is usually placed in a lithotomy position (the patient is on his back) with the knees spread apart and the feet elevated above the head. The patient is suitably prepared for surgery following the hospital guidelines for open surgical procedures.

The surgeon orients the penis for insertion of the probe 42. The probe 42 is sized for insertion into the urethra, is resistant to bending, and is unable to transition past the junction J where the horizontal urethra transitions to the vertical urethra attached to the bladder. The prostate is illustrated between the junction J and the bladder, although it is to be understood that many patients have undergone a prostatectomy and do not have a prostate gland. In any regard, the junction J is that part of the urethra between the horizontal urethra and the vertical urethra that is immediately proximal to the bulbous spongiosis muscle of the bulbar urethra. When the probe 42 is inserted into the urethra, the end 56 is insertable as far as the junction J and no farther.

The anterior edge 94 of the template 44 is sized for placement adjacent to or around the base of the scrotum, and the posterior edge 96 of the template 44 is sized for placement adjacent to or around a portion of the anus.

One or both of the end 56 of the probe 42 and the template 44 is magnetized. For example, in one embodiment the end 56 of the probe 42 includes a magnet and the template includes a magnet, where these two magnets attract each other. In one embodiment the end 56 of the probe 42 includes a magnet and the template includes a metal area that is non-magnetic but attracted to the magnet of the end 56. In one embodiment the end 56 of the probe 42 includes a metal that is attracted to a magnet provided by the template.

Figure 11:
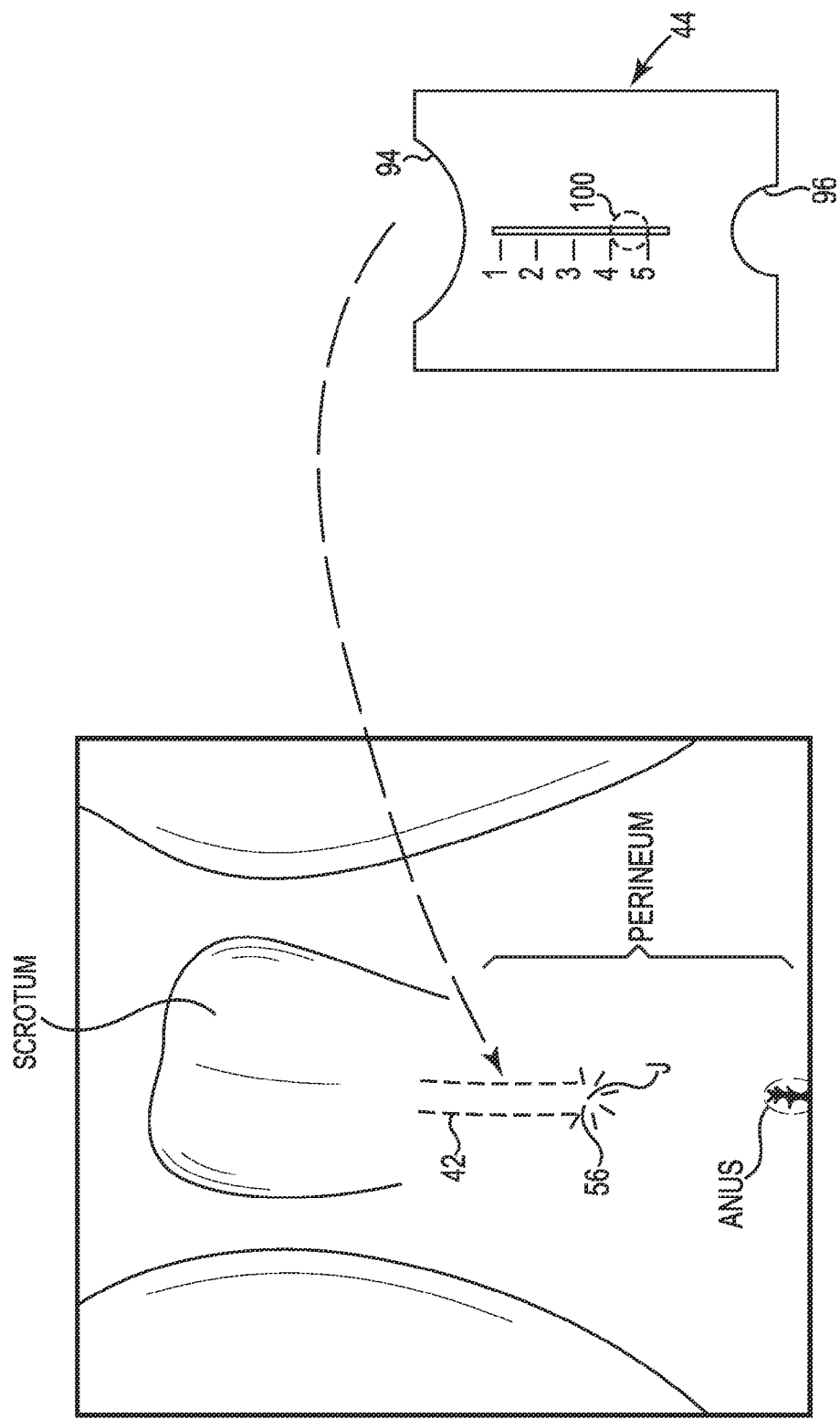
FIG. 11 is a schematic view of the perineal area of the male anatomy with the intra-urethral probe inserted in the urethra and a top view of the template illustrated in FIG. 6.

FIG. 11 is a schematic view of the probe 42 inserted into the urethra until the magnetized end 56 locates the junction J. The probe 42 has followed the horizontal section of the urethra from the glans penis to the bend in the urethra, as indicated by the end 56. The urethra bends at the junction J location ("into the paper" as illustrated if FIG. 11, and as such, the remaining proximal urethra is not visible). The probe 42 is inside the urethra and is thus superior to the skin of the perineum. The magnetic end 56 produces a magnetic field that can be sensed from the perineal area. The magnetic region 100 of the template 44 is configured to be magnetically attracted to the magnetic end 56 of the probe 42, which identifies the junction J as the desired location for an incision.

Figure 12:
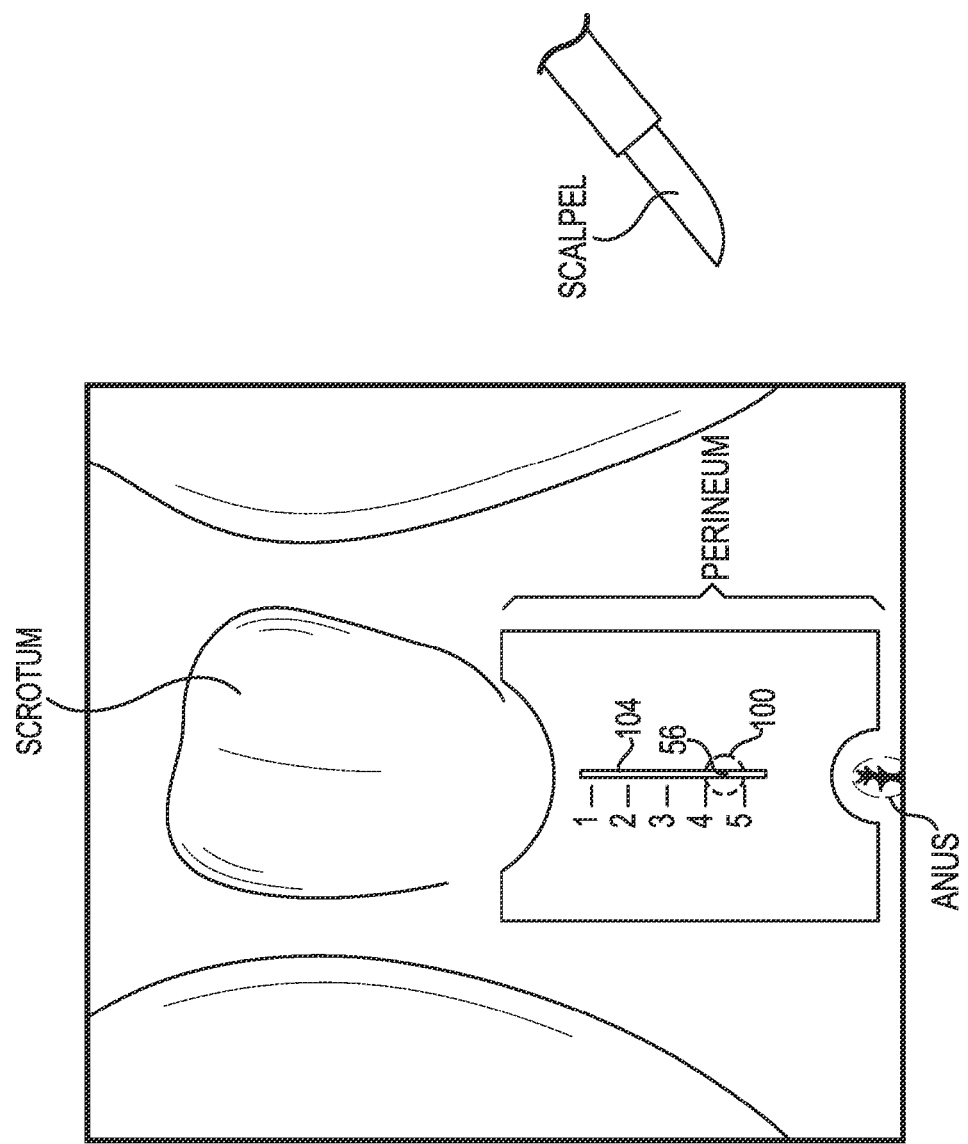
FIG. 12 is a schematic view of the intra-urethral probe and the template employed to identify an incision site in the perineum.

FIG. 12 is a schematic view of the template 44 placed on the perineum between the scrotum and the anus with the magnetic region 100 magnetically attracted to and aligned with the magnetic end 56 of the probe 42. The opening 104 extends through the magnetic region 100 and provides access for a scalpel to place an incision in the perineum, as identified by the attraction of the magnetic region 100 to the magnetic end 56 of the probe 42.

The probe 42 and the template 44 have been employed to identify a desired and optimum incision site for placement of an incision through the perineal tissue to identify the junction J of the urethra suitable for implantation of an AUS. The probe 42 is removed after the incision site is identified, for example by marking with ink or by incising into the skin.

Thereafter, the surgeon will place a urinary catheter (such as a Foley catheter) into the bladder through the urethra to drain urine from the bladder.

Figure 13:
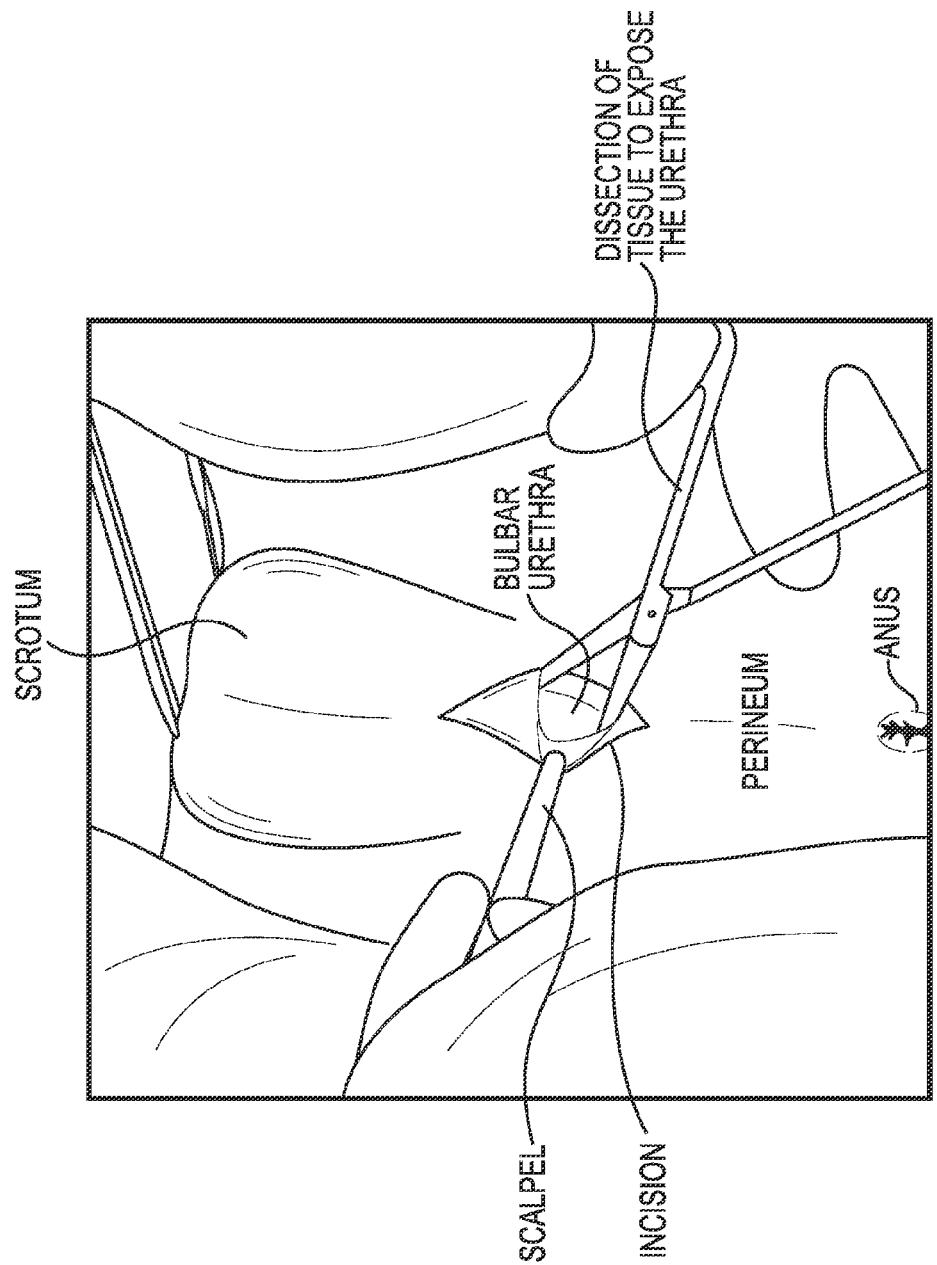

FIG. 13 is a schematic view of the scalpel and a dissection tool employed to dissect tissue through the perineum to expose the bulbar urethra.

FIG. 14 is a schematic view of the urinary catheter place inside the bladder through the urethra to drain urine from the bladder. The surgeon has dissected tissue away from and around the urethral bulb for the suitable placement of a cuff 108 of the AUS.

FIG. 15 is a schematic view of the cuff 108 placed around the urethral bulb of the patient.

Embodiments provide a surgical system adapted for identifying an incision site for the placement of an AUS. The system includes an intra-urethral probe having a distal end that is insertable into a urethra of a patient and a template operable to sense the location of the distal end of the probe. The probe is sized and configured to prevent the distal end of the probe from entering a bladder of the patient, and the distal end of the probe is magnetized to a first polarity. The template is sized for placement between an anus and a scrotum of the patient and is magnetically attractable to the probe.

Although specific embodiments have been illustrated and described in this patent application, it will be appreciated by those of ordinary skill in the art that a variety of alternate and/or equivalent implementations may be substituted for the specific embodiments shown and described without departing from the scope of the invention. This patent application is intended to cover any adaptations or variations of medical devices, as discussed above. Therefore, it is intended that this invention be limited only by the claims and their equivalents.

What is claimed is:

1. A method of identifying an incision site for implantation of an artificial urinary sphincter (AUS), the method comprising:
   inserting a magnetized distal end of a probe into a urethra of a patient;
   placing a template on perineal skin and magnetically attracting a magnetic region of the template to the magnetized distal end of the probe; and
   forming an incision in the perineal skin at a location where the magnetic region of the template is magnetically attracted to the distal end of the probe.

2. The method of claim 1, further comprising:
   preventing the magnetized distal end of the probe from entering a bladder of the patient.

3. The method of claim 1, comprising inserting the magnetized distal end of the probe into the urethra of the patient to a junction in the urethra, with the junction in the urethra located where the urethra transitions from a horizontal orientation extending along a length of a penis to a vertical orientation where the urethra connects with a bladder.

* * * * *